(12) United States Patent
Wang et al.

(10) Patent No.: US 9,089,279 B2
(45) Date of Patent: Jul. 28, 2015

(54) ION-BASED BREATH ANALYSIS SYSTEM

(75) Inventors: Xuefeng Wang, Niskayuna, NY (US); Bo Li, Rexford, NY (US); Cheng-Po Chen, Niskayuna, NY (US); Rui Chen, Clifton Park, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 361 days.

(21) Appl. No.: 13/340,401

(22) Filed: Dec. 29, 2011

(65) Prior Publication Data
US 2013/0168548 A1 Jul. 4, 2013

(51) Int. Cl.
*A61B 5/08* (2006.01)
*G01N 33/497* (2006.01)
*G01N 27/62* (2006.01)

(52) U.S. Cl.
CPC .............. *A61B 5/082* (2013.01); *G01N 33/497* (2013.01); *G01N 27/622* (2013.01); *G01N 27/624* (2013.01)

(58) Field of Classification Search
USPC ........................................................ 250/288
See application file for complete search history.

(56) References Cited

U.S. PATENT DOCUMENTS

| | | | |
|---|---|---|---|
| 4,413,185 A | | 11/1983 | Leveson et al. |
| 5,174,959 A | * | 12/1992 | Kundu et al. ................. 422/413 |
| 5,425,374 A | * | 6/1995 | Ueda et al. .................... 600/532 |
| 6,794,645 B2 | | 9/2004 | Kanik et al. |
| 6,828,552 B2 | | 12/2004 | Hartley |
| 6,868,853 B1 | | 3/2005 | Nilsson et al. |
| 7,576,319 B2 | | 8/2009 | Miller et al. |
| 7,812,396 B2 | | 10/2010 | Kito et al. |
| 7,855,360 B2 | | 12/2010 | Fernandez de la Mora et al. |
| 7,956,323 B2 | | 6/2011 | Morley et al. |
| 2004/0035183 A1 | * | 2/2004 | O'Brien et al. ............... 73/23.36 |
| 2004/0136872 A1 | * | 7/2004 | Miller et al. .................... 422/83 |
| 2005/0065446 A1 | * | 3/2005 | Talton ........................... 600/529 |
| 2005/0085740 A1 | * | 4/2005 | Davis et al. .................... 600/532 |
| 2006/0151687 A1 | * | 7/2006 | Miller et al. .................... 250/282 |
| 2006/0255255 A1 | * | 11/2006 | Miller et al. .................... 250/281 |
| 2007/0167853 A1 | * | 7/2007 | Melker et al. ................. 600/532 |
| 2008/0045825 A1 | * | 2/2008 | Melker et al. ................. 600/365 |
| 2009/0230300 A1 | * | 9/2009 | Trevejo et al. ................ 250/282 |
| 2009/0275852 A1 | * | 11/2009 | Oki et al. ...................... 600/532 |

OTHER PUBLICATIONS

Vautz et al., "Breath-analysis-performance and potential of ion mobility spectrometry", J. Breath Res. 3 (2009) 036004 (8pp).
Perl et al., "Determination of serum propofol concentrations by breath analysis using ion mobility spectrometry", British Journal of Anaesthesia 103 (6): 822-7 (Nov. 3, 2009).

* cited by examiner

*Primary Examiner* — Phillip A Johnston
*Assistant Examiner* — Sean Luck
(74) *Attorney, Agent, or Firm* — Fletcher Yoder, P.C.

(57) ABSTRACT

Disclosed embodiments include systems for analyzing the breath of a patient for the presence of one or more analytes of interest. The systems may include an ion detection system capable of receiving a gas mixture having an analyte of interest expired by a patient, flowing the gas mixture, and ionizing molecules within the gas mixture. The molecules include at least the analyte of interest. The ion detection system is also capable of detecting the ionized analyte of interest.

26 Claims, 5 Drawing Sheets

ION-BASED BREATH ANALYSIS SYSTEM

BACKGROUND

In the field of medicine, it is common practice to administer pharmaceutical agents to a patient for various purposes, such as sedation, pain management, the manipulation of various physiological processes, and so on. Often, the dosage of such agents is monitored via a patient's response to the administered agent. For example, during surgery, a patient may be administered a local or a general anesthetic agent. In situations of general anesthesia, a number of physiological characteristics of the patient may be measured to ensure proper dosage. For example, the patient's heart rate, blood pressure, inspired and expired oxygen, expired carbon dioxide, oxygen saturation in the patient's blood, and similar parameters may be measured. Additionally, in some situations, electroencephalography (EEG) may be performed to measure the patient's consciousness.

Accordingly, a variety of patient responses may be monitored as a result of administering certain agents. Furthermore, while the pharmacokinetics of a particular agent may generally be understood, the rate at which such agents are expelled from the body may vary from patient to patient. Typically, the rates at which certain agents, such as anesthetic agents, are expelled from patients are estimated based upon modeling approaches. For example, such modeling approaches may model the metabolism/expulsion of a certain agent based upon a patient's age, weight, height, gender, and/or other factors. In situations in which a patient is under sedation for extended periods of time, such as during a surgery, the anesthetic agent may be administered in doses according to an output of a model for the particular agent used.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a breath analysis system is provided. The system includes a preparation system, having a first inlet configured to receive a patient's expired breath including an analyte of interest, a second inlet configured to receive a carrier gas, and a mixing chamber configured to mix at least a portion of the patient's expired breath with the carrier gas to generate a gas mixture. The system also includes an ion detection system operatively coupled to the preparation system, the ion detection system having a gas path configured to flow the gas mixture, an ionization source disposed along the gas path and configured to ionize at least the analyte of interest within the gas mixture, and an ion detector disposed along the gas path downstream from the ionization source and configured to detect the ionized analyte of interest.

In another embodiment, a breath analysis system is provided. The system includes an ion detection system having an inlet configured to receive a gas mixture having an analyte of interest expired by a patient, a gas path configured to flow the gas mixture, and an ionization source disposed along the gas path and configured to ionize molecules within the gas mixture. The molecules include at least the analyte of interest. The ion detection system also includes an ion detector disposed along the gas path downstream from the ionization source. The ion detector is configured to detect the ionized analyte of interest.

In a further embodiment, a breath analysis system is provided. The system includes an ion detection system having a substrate with one or more thru holes configured to enable the breath analysis system to integrate onto a circuit board. The substrate includes an inlet configured to receive a gas mixture having an analyte of interest from a patient's expired breath and a gas path fluidly coupled to the inlet and formed within the substrate. The gas path is configured to flow the gas mixture within the substrate toward an outlet of the substrate. The ion detection system also includes an ionization source coupled to the substrate and disposed along the gas path. The ionization source is configured to ionize at least the analyte of interest within the gas mixture. The ion detection system further includes an ion filter coupled to an inner surface of the substrate along the gas path and configured to separate the ionized analyte of interest from other components of the gas mixture. The ion detection system further includes an ion detector coupled to the inner surface of the substrate along the gas path and downstream from the ion filter. The ion detector is configured to generate a signal in response to detecting the presence of the ionized analyte of interest.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Figure 1:
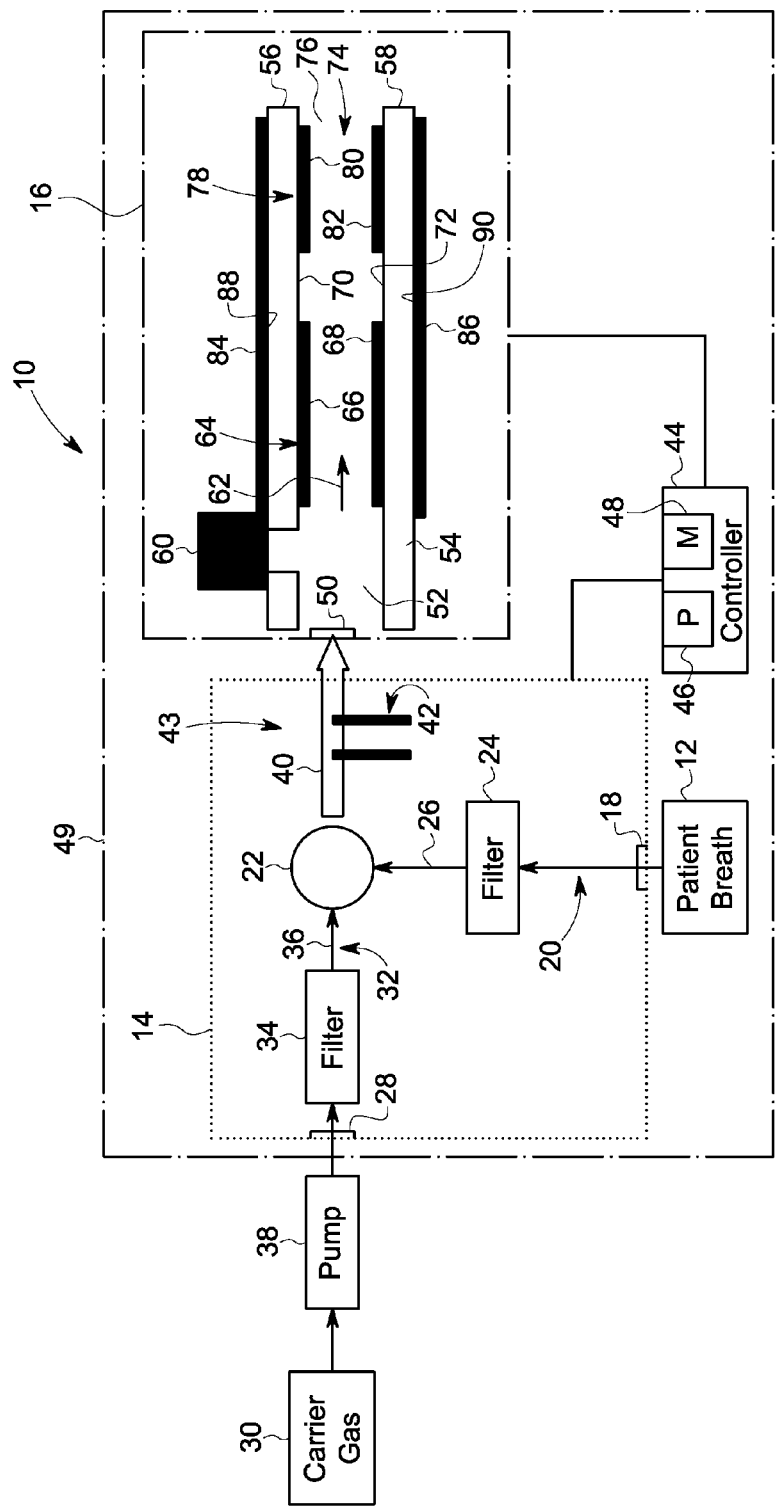
FIG. 1 is a schematic illustration of an embodiment of a breath analysis system having a breath sample preparation system and an ion detection system, in accordance with an aspect of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As noted above, modeling approaches may be utilized to determine appropriate dosages for certain pharmaceutical agents administered to a patient. These models may estimate the appropriate dosages based on a number of factors including, but not limited to the patient's age, weight, height, gender, and/or other factors. However, such modeling approaches may be insufficient or subject to further improvement, as certain patients may not conform to one or more models for a particular agent. Accordingly, it is now recognized that it may be desirable to directly monitor a patient's expulsion of a given pharmaceutical agent, such as an anesthetic agent, by monitoring a concentration of the target agent, or metabolites thereof, within a patient's expired (i.e., exhaled) breath.

Indeed, in accordance with present embodiments, a breath analysis system may include features for receiving and preparing a patient's breath for analysis. The system may, therefore, include features for maintaining the patient's breath within a certain set of parameters, such as temperature, humidity levels, sufficient for analysis. The patient's breath, which contains a target agent (e.g., an anesthetic agent and/or a metabolite thereof), may then be monitored. For example, the breath may be analyzed based on various ion detection methods by first analyzing the breath, filtering the ionized target agent from other ionized molecules, and detecting an amount of the ionized target agent. From this amount, a concentration of the target agent within the patient's breath may be obtained. A caregiver may, therefore, have an accurate measurement of a rate of expulsion of the agent for each individual patient.

With the foregoing in mind, FIG. 1 is a schematic representation of one such embodiment of a breath analysis system 10 for detecting one or more analytes of interest within a patient's expired breath. While the system 10 may be applicable to the detection of any one or a combination of analytes of interest in a patient's breath 12, system 10 may be particularly useful for the detection of analytes of interest resulting from the administration of pharmaceutical agents into a patient's bloodstream. For example, system 10 may be useful for monitoring the presence of intravenously administered anesthetic agents, metabolites of anesthetic agents, analgesics and/or metabolites thereof, pain medication and/or metabolites thereof, blood thinners, etc, within a patient's bloodstream. Indeed, any pharmaceutical agent that may be present within a patient's bloodstream and exhaled through the patient's breath may be detected. In one embodiment, the analyte of interest may include propofol and/or metabolites thereof.

The system 10 includes a breath preparation system 14, which is generally configured to prepare the patient's breath 12 for analysis. The system 10 also includes an ion detection system 16, which is generally configured to ionize and detect one or more parameters of an analyte within the patient's breath. By way of non-limiting example, the one or more parameters may include an amount of the analyte, an estimated concentration of the analyte based on the total volume of breath exhaled by the patient, or similar parameters. Furthermore, the ion detection system 16 may be configured to measure a mass-to-charge ratio of ions detected, such that the system 10 is able to monitor ratios of metabolized agents versus non-metabolized agents, relative concentrations of different agents in embodiments where more than one agent is intravenously administered, and so on. As will be discussed in further detail below, the ion detection system 16 may be configured for ion mobility spectrometry (IMS) or differential mobility spectrometry (DMS).

As illustrated, the breath preparation system 14 includes a breath or first inlet 18, which is configured to receive the patient's breath 12. The first inlet 18, by way of non-limiting example, may include a mouthpiece or similar coupling that a patient may use for injecting, blowing, or otherwise providing to the preparation system 14. The first inlet 18 is configured to introduce the patient's breath 12 into a first flow path 20 from the inlet 18 to a mixing chamber 22. The mixing chamber 22 is discussed in further detail below.

One or more membranes, absorbers, etc., may be disposed along the first flow path 20 to treat the patient's breath 12 before it reaches the mixing chamber 22. By way of non-limiting example, a moisture absorber or filter, a carbon dioxide ($CO_2$) absorber or filter, a temperature sensor and/or a heater, or any combination thereof. The flow path 20 may also be a heated flow path to reduce moisture condensation and breath analytes stiction on the surface of the flow path. In the illustrated embodiment, the breath preparation system 14 includes a breath filter 24, which may represent a single filter/absorber or multiple filters and/or absorbers, configured to remove a substantial portion of water vapor and water, $CO_2$, $O_2$, metabolites, interfering compounds, sputum, food particles, or any combination thereof, from the patient's breath 12. As defined herein, an interfering compound is intended to denote any compound that may interfere with the ionization and/or detection of the analyte of interest. In one embodiment, the breath filter 24 removes at least $CO_2$ and water/water vapor from the patient's breath 12 to facilitate ionization and detection at the ion detection system 16. In another embodiment, the breath filter 24 may contain a gas/vapor separation column to separate the anesthetic agent from other breath compounds based on retention time in the separation column. Thus, the breath filter 24 produces a treated patient breath 26, which may be substantially free of at least $CO_2$ and water/water vapor. The breath preparation system 14, in certain embodiments, may utilize the motive forces arising from the patient's exhalation to motivate the breath 12 through the flow path 20.

The breath preparation system 14 also includes a carrier gas or second inlet 28, which is configured to introduce a carrier gas 30 into the breath preparation system 14. The carrier gas 30, generally, includes any gas that does not interact with the analyte of interest and does not have any substantial effect on the ionization and detection processes performed at the ion detection system 16. By way of non-limiting example, the carrier gas 30 may include air, nitrogen ($N_2$), or noble gases such as helium (He), argon (Ar), and so forth. The carrier gas 30 is then flowed along a second flow path 32, which leads to the mixing chamber 22 mentioned above. As with the flow path 20, one or more features may be disposed along the second flow path 32 for treating carrier gas 30. In the illustrated embodiment, a carrier gas filter 34 is provided along the second flow path 32 to produce a treated carrier gas 36. The carrier gas filter 34 may represent one or more filters and/or absorbers configured to remove impurities that may be associated with commercial sources of the carrier gas 30. For example, the carrier gas filter 34 may remove water/water vapor, $CO_2$, $O_2$, and so on such that the treated carrier gas 36 is substantially free of these impurities. In certain embodiments, the carrier gas 30 may be obtained from a high purity source, such as an ultra high purity source, in which case the filter 34 may not be used.

The carrier gas 30 may be motivated through the second flow path 32 by a pump 38, which may include any pump suitable for use in a fluidic or micro fluidic system. The pump 38 may be integrated into the breath preparation system 14, or may be externally connected to the breath preparation system 14. By way of example, the pump 38 may be fitted directly to the second inlet 28, or may be coupled via one or more channels (e.g., flexible or rigid conduits) to the second inlet 28. The pump 38 may also motivate a gas mixture 40 generated within the mixing chamber 22 through the ion detection system 16.

In the illustrated embodiment, the first and second flow paths 20, 32 converge at the mixing chamber 22. However, any manner by which the first and second flow paths 20, 32 may be coupled to the mixing chamber 22 is presently contemplated. For example, the first and second flow paths 20, 32 may converge into a single channel or conduit before delivery to the mixing chamber 22. The mixing chamber 22 is generally configured to mix the carrier gas 30 (or the treated carrier gas 36) with the treated patient breath 26 to generate the gas mixture 40 having a desired pressure or flow rate. For example, the mixing chamber may be a hollow chamber in which the carrier gas 30/treated carrier gas 36 and the treated patient breath 26 are mixed by flowing in crosswise directions against one another. In another non-limiting example, the mixing chamber 22 may include features to increase the contact area between the carrier gas 30/treated carrier gas 36 and the treated patient breath 26, such as porous membranes, a plurality of spheres or rings, vanes, or any combination thereof. Indeed, any feature for mixing two or more gas flows is presently contemplated for use within the mixing chamber 22.

As noted, as a result of the flow mixing within the mixing chamber 22, the gas mixture 40 is produced, and is sent to the ion detection system 16. In certain embodiments, as illustrated, the breath analysis system 14 may include one or more sensors 42 disposed along a transfer path 43 coupling the breath preparation system 14 with the ion detection system 16. The sensors 42 may be used to measure pressure, humidity, temperature, flow rate, or other parameters of the gas mixture 40. Various operational parameters of the gas mixture 40 may be adjusted as a result of the monitoring performed by the sensors 42. By way of a non-limiting example, it may be desirable to reduce a flow rate of the carrier gas 30 in embodiments where the gas mixture 40 has undesirably high levels of moisture, $CO_2$, etc., to increase an amount of time that the carrier gas 30 interacts with the carrier gas filter(s) 34. Alternatively or additionally, one or more heaters of the gas preparation system 14 may be adjusted based upon a temperature of the gas mixture 40 measured by the sensors 42, for example to maintain the gas mixture 40 within a desired temperature range. In one embodiment, the transfer path 43 is configured to heat the gas mixture 40, maintain a temperature of the gas mixture 40, or a combination thereof, using the sensors 42 and/or one or more heaters of the system 14, which may be disposed along the path 43.

A controller 44 communicatively coupled to the breath preparation system 14 may monitor the information collected by the sensors 42. The controller 44 may also make adjustments to the flow rate of the carrier gas 30 and/or the patient breath 12 by adjusting valves, pump flow rates, and so on. Accordingly, the controller 44 may be a have a processor 46 and a memory 48, the memory 48 having instructions executable by the processor 46 for performing one or more monitoring and/or parameter maintenance routines. Indeed, the memory 48 may by any tangible, machine-readable, non-transitory medium having the instructions that are executable by the processor 46 in the form of stored code. In one embodiment, the controller 44 may be all or a part of an implementation-specific or general purpose computing device having the processor 46 and associated memory 48. The controller 44 may also have a user interface that has a display and a user input interface, such as a keyboard, mouse, touchpad, or other user input device. The display can give information of measured anesthetic concentrations and other patient information. Further, the controller 44 may be integrated into a single circuit board 49 or a single package having the controller 44, the breath preparation system 14, the ion detection system 16, or any combination thereof. Again, the controller 44 is generally configured to maintain the gas mixture 40 within certain conditions suitable for ionization and detection within the ion detection system 16.

As illustrated, the breath preparation system 14 and the ion detection system 16 are fluidly coupled via a gas mixture or third inlet 50. Specifically, the gas mixture 40 flows from the breath preparation system 14, through the third inlet, and into the ion detection system 16. The breath preparation system 14 and the ion detection system 16 may be coupled via a channel or conduit, or an outlet of the breath preparation system 14 may be the third inlet 50. In certain embodiments, the motive forces generated by the pump 38 may provide the motive forces that drive the gas mixture 40 through the ion detection system 16.

The third inlet 50 of the ion detection system 16 leads to a gas path 52 formed within a substrate 54 of the ion detection system 16. By way of example, the substrate 54 of the ion detection system 16 may include one or more layers, where the gas path 52 may be formed by a void between layers of the substrate 54. In the illustrated embodiment, the substrate 54 includes first and second substrate layers 56, 58 on which various components of the ion detection system 16 are integrated. Non-limiting examples of such components are generally illustrated in FIG. 1 and are discussed in further detail below with respect to FIGS. 2 and 5-9.

As illustrated in FIG. 1, the components integrated onto or within the substrate 54 include an ionization source 60 disposed along the gas path 52 and configured to ionize the gas mixture 40 to produce an ionized gas mixture 62. For example, as discussed in further detail below, the ionization source 60 may include any ionization source capable of ionizing at least an analyte of interest contained within the gas mixture 40. By way of non-limiting example, the ionization source 60 may include a UV lamp, a β-emitter, a corona discharge source, a flame ionization source, an electrospray ionization source, a chemical ionization source, or any combination thereof. In certain embodiments, the ionization source 60 may be tuned so as to selectively ionize the analyte of interest within the gas mixture 40. That is, the ionization source 60 may emit a source of ionizing energy (e.g., electromagnetic radiation, a chemical ionization source, a flame) that is at an energy sufficient to overcome the ionization potential of the analyte of interest. In one embodiment, for example, the ionization source 60 may include a UV lamp configured to emit wavelengths of light corresponding to an ionization potential of the analyte of interest (e.g., propofol). Keeping in mind that ionization sources may emit wavelengths within a bandwidth centered at a particular wavelength, such central or peak wavelengths may include, as a non-limiting example, wavelengths below approximately 150 nanometers (nm), such as below 140 nm, below 130 nm, or below 120 nm. In one embodiment, the UV lamp may be tuned to the first ionization potential of an anesthetic agent, such as propofol.

The ion detection system 16 also includes an ion filter 64 having a first ion filter circuit 66 and a second ion filter circuit 68 disposed on a first inner surface 70 of the first substrate layer 56 and a second inner surface 72 of the second substrate layer 58, respectively. The first and second ion filter circuits 66, 68 are, therefore, disposed along the gas path 52, which is defined by the first and second inner surfaces 70, 72. As noted above, the ion detection system 16 may be configured for IMS or DMS. Accordingly, the first and second ion filter circuits 66, 68 may be configured to generate a radiofrequency (RF) electric field, a direct current (DC) electric field, or a combination thereof. In a DMS configuration, the first and second filter circuits 66, 68 may generate an RF electric field, or an RF and DC electric field, while in an IMS configuration, the first and second ion filter circuits 66, 68 may generate only a DC electric field. In the DMS configuration, ions within the ionized gas mixture 62 are separated based upon their differential mobilities within the RF or RF+DC electric field. In the IMS configuration, the filters 66 and 68 may be multiple pairs of electrodes to accelerate the ionized analytes by applying a DC electric field gradient along the electrodes and separate the anlaytes based on their time-of-flight through the detector channel 62. In another embodiment, the ion filter may combine the DMS differential mobility detection and the IMS time-of-flight detection to further improve selectivity and sensitivity.

By way of non-limiting example, the RF electric field generated by the first and second ion filter circuits 66, 68 in a DMS configuration may be an asymmetric waveform at between approximately 1 and 2 megahertz (MHz), such as at approximately 1.0 MHz, 1.1 MHz, 1.2 MHz, 1.3 MHz, 1.4 MHz, 1.5 MHz, 1.6 MHz, 1.7 MHz, 1.8 MHz, 1.9 MHz, or approximately 2.0 MHz. The strength of the RF electric field may be between approximately 10 kiloVolts per centimeter (kV/com) and 40 kV/cm, such as between approximately 15 kV/cm and 35 kV/cm, or between approximately 20 kV/cm and 30 kV/cm. In one embodiment, the strength of the RF electric field may be approximately 30 kV/cm. The strength of the RF field may be varied during operation of the ion detection system 16.

In embodiments in which the first and second filter circuits 66, 68 generate a DC electric field in addition to the RF electric field, the DC electric field may be generated between approximately −800 V/cm and 800V/cm. In some embodiments, the scan may have a duration of between approximately 1 second (s) and 5 s, such as between approximately 2 s and 4 s. In one non-limiting example, the scan may have a duration of approximately 3.8 s. In one embodiment, the ion filter can be used in non-scanning mode, where the DC electric field is fixed to provide continuous detection of a specific analyte, such as propofol.

As the ionized molecules within the ionized gas mixture 62 pass through the ion filter 64, the molecules become separated based on their respective mass, charge, size, shape, or any combination thereof. The respective migration time of each of the ionized molecules through the gas path 52 and to a detection region 74 may be characteristic of their mobility or differential mobility within the electric field generated by the ion filter 64. Therefore, the ion detection system 16, in certain embodiments, may be configured to detect one or more than one analytes of interest.

Specifically the detection region 74, which is disposed along the gas path 52 toward an outlet end 76 of the ion detection system 16, includes a detector 78. Generally, the detector 78 may include any detector circuit capable of detecting the presence of ions. For example, the detector 78 may include one or more electrometers. In accordance with present embodiments, the detector 78 may include a Faraday cup, or a pair of parallel Faraday plates capable of generating a current in response to ions striking a surface of the cup/plates. In the illustrated embodiment, the detector 78 includes first and second detector circuits 80, 82 disposed on the first and second inner surfaces 70, 72, respectively, of the substrate 54. The first and second detector circuits 80, 82 may be configured to measure an amount of ions striking their respective surfaces, a mass-to-charge ratio of the ions, a time at which the ions strike the circuits 80, 82, or any combination thereof. Further, in one embodiment, the controller 44 may be operatively coupled to the detector 78 to monitor a concentration of one or more analytes of interest within the patient breath 12. For example, the ion detection system 16 may be integrated onto the single circuit board 49 having the breath preparation system 14 and the controller 44.

As noted above, the controller 44 may monitor one or more parameters of the gas mixture 40, such as a pressure, temperature, flow rate, moisture level, etc., of the gas mixture 40. Similarly, the controller 44 may monitor and control a temperature within the ion detection system 16 via first and second heater circuits 84, 86. As discussed in further detail below, the first and second heater circuits 84, 86, may include heating circuitry such as resistive heaters, as well as temperature sensing circuitry. As illustrated, the first and second heater circuits 84, 86 are integrated onto a first outer surface 88 and a second outer surface 90, respectively, of the substrate 54.

The first and second heater circuits 84, 86 are generally configured to maintain the temperature of the ion detection system 16 within a desired temperature range. By way of non-limiting example, the first and second heater circuits 84, 86 may maintain a temperature of the ion detection system 16 within a range between approximately 30° C. and 100° C., such as between approximately 40° C. and 90° C., 50° C. and 80° C., or between approximately 60° C. and 70° C. It may be desirable to maintain the temperature of the ion detection system 16 within such ranges (e.g., between approximately 50° C. and 80° C.) to enable sufficient ionization of the gas mixture 40 and detection of the ionized analytes of interest within the ionized gas mixture 62 as the gas mixture 40 flows through the gas path 52. Indeed, it may be desirable, in certain embodiments, for the temperature within the gas path 52 to be maintained within the ranges listed above.

Figure 2:
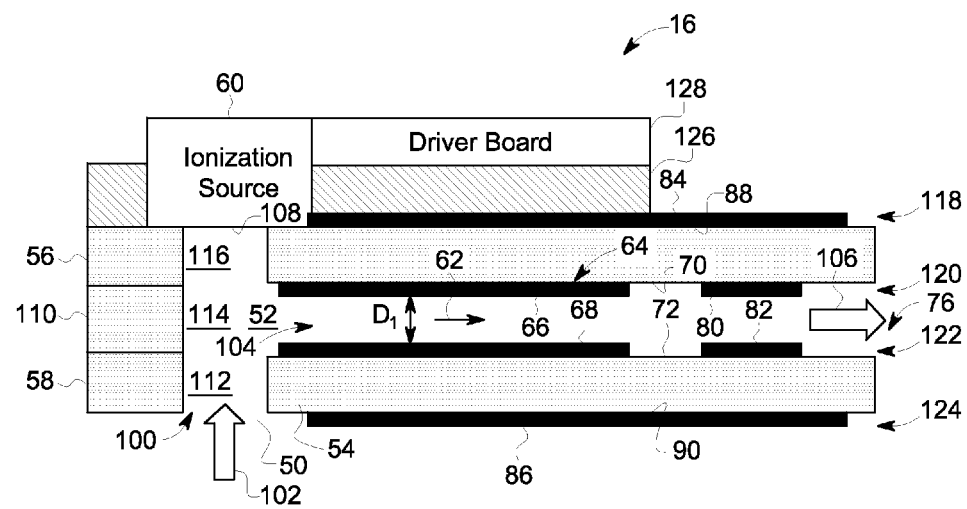
FIG. 2 is a cross-sectional schematic illustration of an embodiment of the ion detection system of FIG. 1, in accordance with an aspect of the present disclosure.

It should be noted that while the gas path 52 of the ion detection system 16 is illustrated as a substantially straight path in FIG. 1, other configurations are also presently contemplated, as illustrated in FIG. 2. Specifically, FIG. 2 illustrates a cross-sectional side view of an embodiment of the ion detection system 16, where the gas path 52 includes a first portion 100 having a first flow direction 102 and a second portion 104 having a second flow direction 106. In FIG. 2, the first and second flow directions 102, 106 are oriented crosswise relative to one another, which may promote homogeneity of the gas mixture 40 by creating turbulent flow. Additionally, the first flow direction 102 flows the gas mixture 40 toward the ionization source 60, rather than past the ionization source 60 as in the embodiment of FIG. 1. The first flow direction 102 may, therefore, enable enhanced ionization of the gas mixture 40 compared to the configuration of FIG. 1. However, in the illustrated configuration, molecules may accumulate on a surface 108 of the ionization source 60. Accordingly, while the embodiment of FIG. 2 may provide enhanced ionization compared to the embodiment of FIG. 1, the embodiment of FIG. 1 may have reduced buildup on the ionization source 60 compared to the embodiment of FIG. 2.

As noted above with respect to FIG. 1, the substrate 54 of the ion detection system 16 may have one or more layers on which various components of the ion detection system 16 are integrated. In the embodiment depicted in FIG. 2, the substrate 54 includes the first and second substrate layers 56, 58, and also includes a third substrate layer 110. The second and third substrate layers 58, 110 each include respective openings 112, 114 corresponding to the inlet 50, while the first substrate layer 56 includes an opening 116 enabling the ionization source 60 to ionize the gas mixture 40. The opening 114 of the third substrate layer 110, which is disposed between the first and second substrate layers 56, 58, also corresponds to the second portion 104 of the gas path 52, which flows the gas mixture 40 from the ionization source 60 to the first and second detector circuits 80, 82. A distance $d_1$ between the first and second inner surfaces 70, 72 of the first and second substrate layers 56, 58 may correspond to the thickness of the third substrate layer 110 and, therefore, the thickness of the second portion 106 of the gas path 52. By way of non-limiting example, the distance $d_1$ may be between approximately 0.1 millimeters (mm) and 1 centimeter (cm), such as approximately 0.1 mm, 0.2 mm, 0.3 mm, 0.4 mm, 0.5 mm, 0.6 mm, 0.7 mm, 0.8 mm, 0.9 mm, or approximately 1.0 mm.

The substrate 54 may be formed from a dielectric or semiconductor material, which may enable the components of the ion detection system 16 to integrate with each other and with the circuit board 49 without shorting. By way of non-limiting examples, the dielectric may include glass, glass fiber reinforced polytetrafluoroethylene (PTFE) composites, ceramic composites such as low temperature cofired ceramics, glass reinforced hydrocarbon/ceramic laminate, or any combination thereof. By way of non-limiting example, the semiconductor material may be silicon. As illustrated, certain components of the ion detection system 16 are integrated onto either the first and second outer surfaces 88, 90, or the first and second inner surfaces 70, 72. Accordingly, the ion detection system 16 includes at least four layers, such as a first layer 118, a second layer 120, a third layer 122, and a fourth layer 124. The first, second, third, and fourth layers 118, 120, 122, 124 are discussed in detail below with respect to FIGS. 5, 6, 8, and 9, respectively.

The ion detection system 16 includes a gasket layer 126, which is configured to seal the substrate 54 and block the gas mixture 40 and/or the ionized gas mixture 62 from escaping the gas path 52. As illustrated, the gasket layer 126 may also seal the ionization source 60 against the substrate 54. A driver board 128 containing the electronics for controlling the ion filter 64 is illustrated as positioned against the gasket 126.

Figure 3:
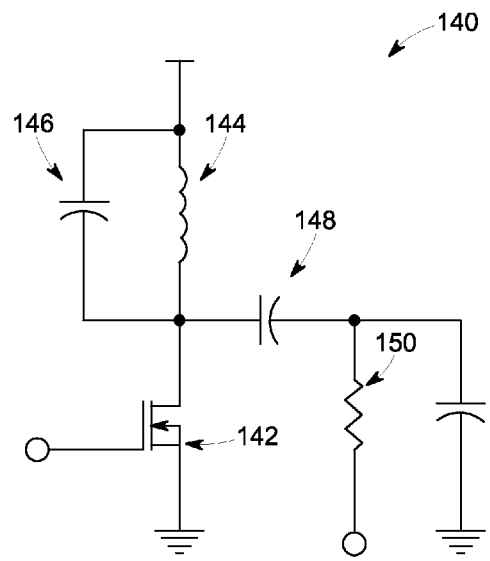
FIG. 3 is a circuit diagram of an embodiment of a driver circuit for the ion filter circuit of FIG. 2, in accordance with an aspect of the present disclosure.
Figure 4:
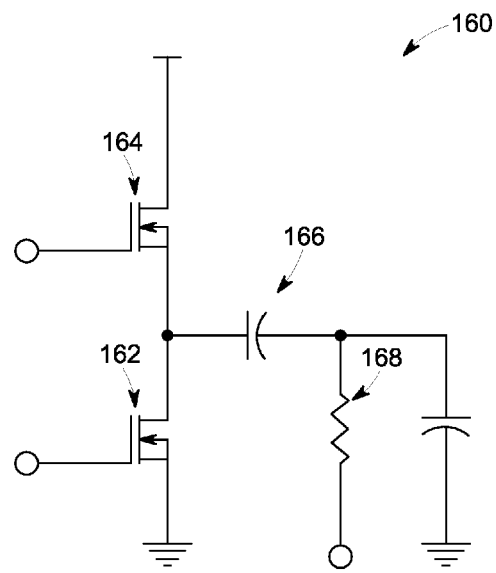
FIG. 4 is a circuit diagram of an embodiment of a driver circuit for the ion filter circuit of FIG. 2, in accordance with an aspect of the present disclosure.

The driver board 128 may include a variety of configurations tailored to the particular type of ion filtering performed by the ion detection system 16 (e.g., DMS vs. IMS), the voltage sources available to the breath analysis system 10, and/or similar considerations. Embodiments of the electronic circuitry for driving the ion filter 64 are illustrated in FIGS. 3 and 4. In particular, FIG. 3 illustrates a flyback RF driver circuit 140 and FIG. 4 illustrates a half-bridge RF driver circuit 160.

The flyback RF driver circuit 140 of FIG. 3 includes a first transistor 142, which is turned on and off to control the voltages applied to the ion filter 64. In the illustrated embodiment, the first transistor 142 has a single control signal input to generate high voltage pulses for the ion filter 64. A loading inductor 144 and a first capacitor 146 form an energy storage element. The energy storage element is charged up when the first transistor 142 is turned on, and discharges through a second capacitor 148 when the first transistor 142 is turned off. This charge transfer action raises the voltage on the ion filter 64 higher than a supply voltage provided to the driver circuit 140. A separate DC bias voltage is applied through a first resistor 150 to shift the overall voltage waveform applied to the ion filter 64.

As noted above, FIG. 4 depicts an embodiment of the half-bridge RF driver circuit 160. The half-bridge driver circuit 160 includes first and second transistors 162, 164 having two complementary control signals to generate high voltage pulses for the ion filter 64. The second transistor 164 is turned on to raise the voltage on the ion filter 64 through a first capacitor 166. The second transistor 164 is turned off after a specified delay, and the first transistor 162 is subsequently turned on to discharge the ion filter 64. The supply voltage of the half-bridge driver circuit 160 determines the voltage level applied to the ion filter 64. RF voltage pulses can be precisely controlled by the complementary control signals. As in FIG. 3, a separate DC bias voltage is applied through a first resistor 168 to shift the overall voltage waveform applied to the ion filter 64.

Figure 5:
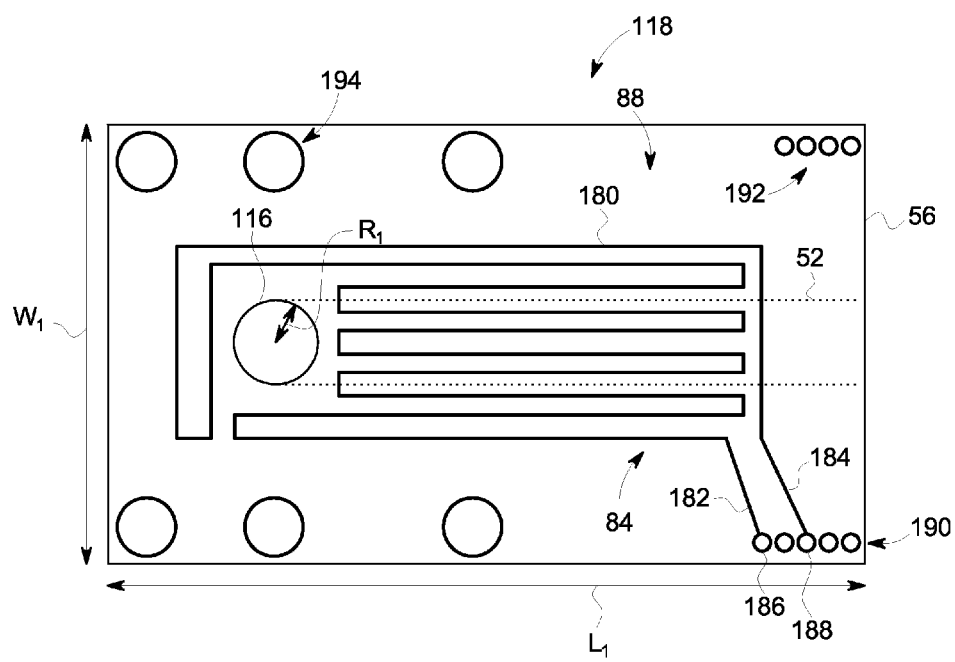
FIG. 5 is a schematic top view of an embodiment of a layer of the ion detection system having a resistive heater for temperature control of a gas flow path, in accordance with an aspect of the present disclosure.

As noted above with respect to FIG. 2, the driver board 128 may be disposed over the first layer 118 of the ion detection system 16. A schematic top view of one embodiment of the first layer 118 is illustrated in FIG. 5. The first layer 118, as noted above, is formed from the integration of the first heater circuit 84 onto the first outer surface 88 of the first substrate layer 56. The first heater circuit 84, as illustrated, includes a resistive coil 180 printed or otherwise disposed onto the first substrate layer 56. The resistive coil 180 is positioned over the gas path 52 to enable temperature maintenance of the gas mixture 40 and the ionized gas mixture 62 to reduce temperature effects on the ionization, mobility, and detection processes discussed above. The first heater circuit 84 also includes first and second conductors 182, 184 configured to couple the resistive coil 180 with a current source, such as a current source disposed on the main circuit board 49 and/or a heater of the fourth layer 124, as discussed below.

In the illustrated embodiment, the first and second conductors 182, 184 of the first heater circuit 84 are routed through first and second plated thru holes 186, 188 of a first plurality of thru holes 190. As discussed in further detail below, the first substrate layer 56 also includes additional thru holes in the first plurality of thru holes 190 and a second plurality of thru holes 192. The first and second pluralities of thru holes 190, 192 are generally configured to enable the electronics of the first, second, third, and fourth layers 118, 120, 122, 124 to electrically couple with one another and/or with the circuit board 49. In certain embodiments, the first plurality of thru holes 190 are configured to enable electrical coupling between active circuits, i.e., heaters, detectors, and filters of the ion detection system 16 with each other and/or the circuit board 49, while the second plurality of thru holes 192 enable electrical coupling between the sensors of the ion detection system 16 and the circuit board 49.

The illustrated first substrate layer 56 also includes a plurality of mounting thru holes 194. The plurality of mounting thru holes 194 may traverse the first, second, third, and fourth layers 118, 120, 122, 124 to enable them to physically couple to one another and also to the circuit board 49. The plurality of mounting thru holes 194 may be plated.

The first substrate layer 56, as noted above with respect to FIG. 2, also includes the opening 116, which is configured to enable the ionization source 60 (FIG. 2) to ionize the gas mixture 40. As illustrated in FIG. 5, the opening 116 is a circular-shaped opening having a radius $R_1$. By way of non-limiting example, the radius $R_1$ may be between approximately 1 mm and 5 mm, such as approximately 1 mm, 2 mm, 2.5 mm, 3 mm, 4 mm, or 5 mm. Other shapes are also presently contemplated for the opening 116. Indeed, any the opening 116 may have shape that enables ionization of the gas mixture 40 by the ionization source 60. For example, the opening 116 may have a square, rectangular, or any polygonal shape, or may be semi-circular, elliptical, or any rounded shape.

Furthermore, while the ion detection system 16 may have any size and shape, in accordance with certain of the present embodiments, the ion detection system 16 may be sized to fit onto the circuit board 49. Indeed, in one embodiment, the entire breath analysis system 10, as mentioned above with respect to FIG. 1, may be integrated onto the circuit board 49 to enable enhanced portability. In FIG. 5, the first substrate layer 56, which may have similar or substantially the same dimensions as the second and third substrate layers 58, 110, is rectangular in shape. However, it should be noted that any shape is presently contemplated for the first, second, and third substrate layers 56, 58, 110. By way of non-limiting example, rectangular, square, or any polygonal shapes are presently contemplated. In the illustrated embodiment, the first substrate layer 56 (and the second and third substrate layers 58, 110) is rectangular, and includes a length $L_1$ and a width $W_1$. Again, while any size is presently contemplated for the substrate layers, by way of non-limiting example the length $L_1$ may be between approximately 25 mm and 50 mm, such as approximately 25 mm, 30 mm, 35 mm, 40 mm, 45 mm, or 50 mm. In one embodiment, the length $L_1$ may be approximately 30.5 mm. Similarly, while any size is presently contemplated for the substrate layers, by way of non-limiting example the width $W_1$ may be between approximately 15 mm and 30 mm, such as approximately 15 mm, 20 mm, 25 mm, or 30 mm.

Figure 6:
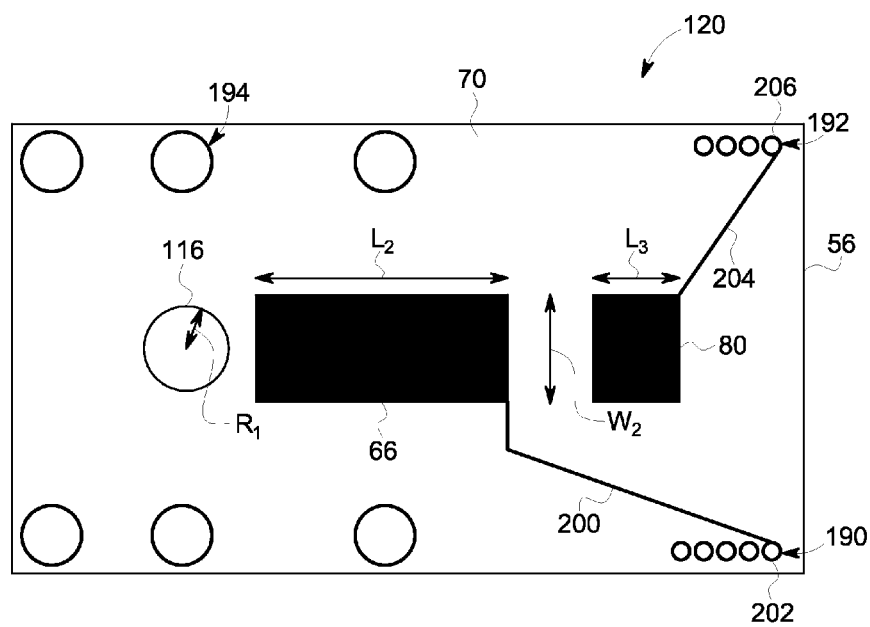
FIG. 6 is a schematic top view of an embodiment of a layer of the ion detection system having an ion filter circuit for separation ions within an ionized gas mixture flowing through the ion detection system and an ion detector for detecting at least an ionized analyte of interest, in accordance with an aspect of the present disclosure.

An embodiment of the second layer 120, which includes the electronics of the ion detection system 16 disposed on the first inner surface 70 of the first substrate layer 56, is illustrated in a schematic top down view in FIG. 6. As with the first layer 118 of FIG. 5, the second layer 120 includes the first and second pluralities of thru holes 190, 192, and the plurality of mounting thru holes 194. The second layer 120 also includes the first ion filter circuit 66, which may be an electrode, a coil, or other circuit that contributes to the production of an electric field for separating an ionized analyte of interest (e.g., an ionized pharmaceutical agent) from other molecules of the ionized gas mixture 62. The first ion filter circuit includes a first conductor 200, which is routed through a third plated thru hole 202, through the remaining layers of the ion detection system 16, and to the circuit board 49 and/or to the driver board 128.

The first ion filter circuit 66 has a length $L_2$ that enables the production of an electric field of sufficient size to interact with and separate various ionized molecules of the ionized gas mixture 62. While any length $L_2$ is presently contemplated, by way of non-limiting example, the length $L_2$ may be between approximately 5 and 20 mm. For example, the length $L_2$ may be approximately 5 mm, 10 mm, 15 mm, or 20 mm. A width $W_2$ of the first ion filter circuit 66 may be substantially equal to a width of the first detector circuit 80. In certain embodiments, the width $W_2$ may also be substantially equal to a width of the gas path 52, which is discussed in further detail below with respect to FIG. 7. While any width $W_2$ is presently contemplated, by way of non-limiting example the width $W_2$ may be between approximately 5 mm and 10 mm, such as approximately 5 mm, 6 mm, 7 mm, 8 mm, 9 mm, or 10 mm.

The second layer 120 also includes the first detector circuit 80, which may be a Faraday plate configured to produce a current in response to receiving ions (e.g., the ionized analyte of interest). The first detector circuit 80 may be coupled to the circuit board 49 or another device via conductor 204, which is routed through a fourth plated thru hole 206 of the second plurality of thru holes 192. As noted above, the first detector circuit 80 and the first ion filter circuit 66 are disposed along the gas path 52 for interacting with the ionized gas mixture 62. Further, any length of the first detector circuit 80 is presently contemplated. By way of non-limiting example, a length $L_3$ of the first detector circuit 80 may be between approximately 1 mm and 10 mm, such as approximately 1 mm, 2 mm, 3 mm, 4 mm, 5 mm, 6 mm, 7 mm, 8 mm, 9 mm, or 10 mm.

Figure 7:
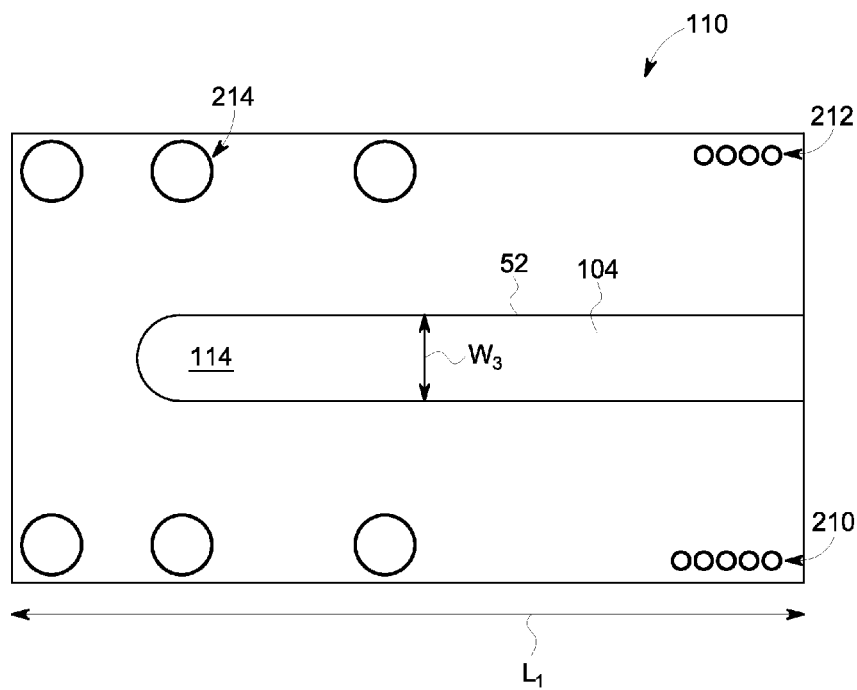
FIG. 7 is a schematic top view of an embodiment of a spacing layer of the ion detection system having an opening corresponding to a gas path of the ion detection system, in accordance with an aspect of the present disclosure.

As noted above with respect to FIG. 2, the ion detection system 16 includes the third substrate layer 110, which is positioned between the first and second substrate layers 56, 58. One embodiment of the third substrate layer 110 is depicted in FIG. 7, which is a schematic top view. In the illustrated embodiment, the third substrate layer 110 includes a first plurality of plated thru holes 210, which correspond to the respective positions of the first plurality of plated thru holes 190 of the first substrate layer 56, and a second plurality of plated thru holes 212, which correspond to the respective positions of the second plurality of plated thru holes 192 of the first substrate layer 56. The third substrate layer 110 also includes a plurality of mounting holes 214, which correspond to the respective positions of the plurality of mounting holes 194 of the first substrate layer 56. Indeed, as noted above, the first and second pluralities of plated thru holes are generally configured to enable electrical connections between the layers of the ion detection system 16, while the mounting holes are configured to enable mounting of the ion detection system 16 to the circuit board 49.

The third substrate layer 110, as noted above, also includes the opening 114, which corresponds to the positioning of the ionization source 60 and the gas path 52. Again, the opening 114 generally defines at least the second portion 104 of the gas path 52. Indeed, in embodiments where the gas path 52 is substantially straight through the ion detection system 52 (i.e., does not have crosswise flow directions), the opening 114 may span the entire length $L_1$ of the third substrate layer 110. Furthermore, as noted above with respect to FIG. 6, in certain embodiments a width $W_3$ of the gas path 52, i.e., the opening 114, may be substantially equal to the width $W_2$ of the first ion filter circuit 66 and the first detector circuit 80. However, embodiments where $W_2$ and $W_3$ are different are also presently contemplated. For example, the gas path 52 may be wider than the first ion filter circuit 66, or the first detector circuit 80, or both, or may be smaller than the first ion filter circuit 66, or the first detector circuit 80, or both.

Figure 8:
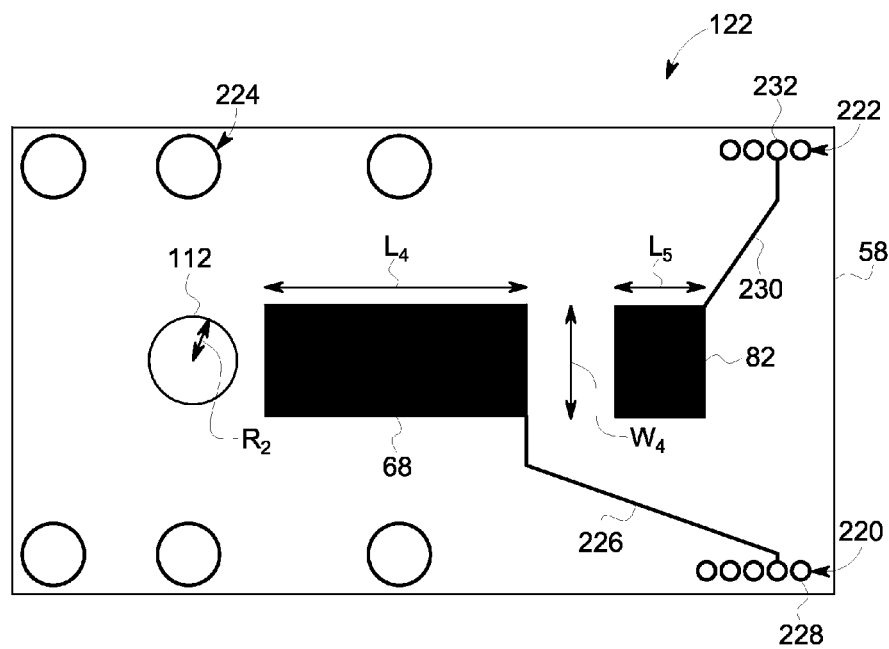
FIG. 8 is a schematic top view of an embodiment of a layer of the ion detection system having an ion filter circuit for separation ions within an ionized gas mixture flowing through the ion detection system and an ion detector for detecting at least an ionized analyte of interest, in accordance with an aspect of the present disclosure.
Figure 9:
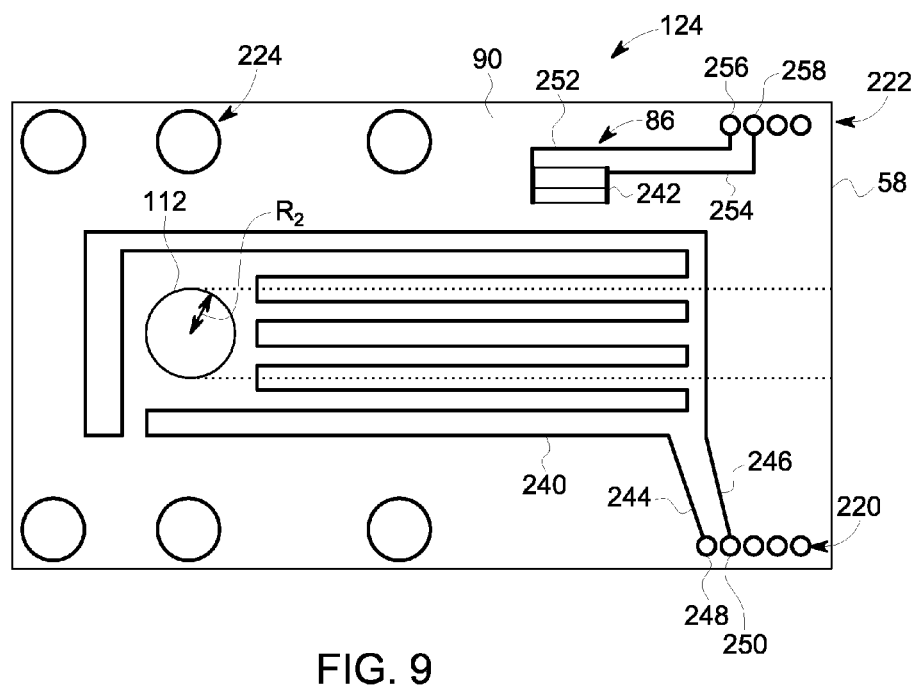
FIG. 9 is a schematic top view of an embodiment of a layer of the ion detection system having a resistive heater and a temperature sensor for temperature control of the ion detection system, in accordance with an aspect of the present disclosure.

An embodiment of the third layer 122 of the ion detection system 16 is illustrated in FIG. 8. Specifically, FIG. 8 is a schematic top view of an embodiment of the third layer 122 having the second ion filter circuit 68, the second detector circuit 82, and first and second plated pluralities of plated thru holes 220, 222. The first and second plated pluralities of plated thru holes 220, 222, in accordance with present embodiments, correspond to the respective positions of the plated thru holes of the first and second layers 118, 120.

As illustrated, the second ion filter circuit 68 is coupled to a conductor 226, which is routed through a first plated thru hole 228 for coupling to the circuit board 49 and/or to the driver board 128. Similarly, the second detector circuit 82 is coupled to a second conductor 230, which is routed through a second plated thru hole 232 and to the circuit board 49.

Regarding the dimensions of the second ion filter circuit 68 and the second detector circuit 82, their size may be substantially the same as the dimensions discussed above with respect to the first ion filter circuit 66 and the first detector circuit 80, respectively. Alternatively, the second ion filter circuit 68 and the second detector circuit 82 may have dimensions that are different than the dimensions discussed above. Generally, the second ion filter circuit 68 has a length $L_4$ that enables the production of an electric field of sufficient size to interact with and separate various ionized molecules of the ionized gas mixture 62. While any length $L_4$ is presently contemplated, by way of non-limiting example, the length $L_4$ may be between approximately 5 and 20 mm. For example, the length $L_4$ may be approximately 5 mm, 10 mm, 15 mm, or 20 mm.

A width $W_4$ of the first ion filter circuit 68 may be substantially equal to a width of the second detector circuit 82. In certain embodiments, the width $W_4$ may also be substantially equal to the width $W_3$ of the gas path 52. While any width $W_4$ is presently contemplated, by way of non-limiting example, the width $W_4$ may be between approximately 5 mm and 10 mm, such as approximately 5 mm, 6 mm, 7 mm, 8 mm, 9 mm, or 10 mm.

Generally, the second detector circuit 82 may have a length $L_5$ that is sufficient for contacting most or all of the ionized molecules within the ionized gas mixture 62. Indeed, any length $L_5$ is presently contemplated. By way of non-limiting example, the length $L_5$ of the second detector circuit 82 may be between approximately 1 mm and 10 mm, such as approximately 1 mm, 2 mm, 3 mm, 4 mm, 5 mm, 6 mm, 7 mm, 8 mm, 9 mm, or 10 mm.

The third layer 122 also includes a plurality of mounting holes 224. The plurality of mounting holes 224 generally correspond to the respective positions of the mounting holes of the first and third substrate layers 56, 110. Indeed, the plurality of mounting holes 224 are generally configured to enable physical coupling between the first, second, and third substrate layers 56, 58, 110, and the circuit board 49.

The second substrate layer 58, as noted above with respect to FIG. 2, also includes the opening 112, which may be an unplated thru hole. As discussed with respect to FIG. 2, the opening 112 may serve as the inlet 50 for the gas mixture 40. The opening 112 may have a radius $R_2$ that enables sufficient influx of the gas mixture 40 while enabling the ionization source 60 to ionize a sufficient number of target molecules within the gas mixture 40. While any radius $R_2$ is presently contemplated, by way of non-limiting example the radius $R_2$ may be between approximately 1 and 5 mm, such as approximately 1 mm, 2 mm, 2.5 mm, 3 mm, 4 mm, or 5 mm. The radius $R_2$ may or may not be substantially equal to the radius $R_1$ of FIGS. 5 and 6.

As noted above with respect to FIG. 2, the second outer surface 90 of the second substrate layer 58, with its associated electronics, forms the fourth layer 124 of the ion detection system 16. An embodiment of the fourth layer 124 is depicted schematically in FIG. 9. As illustrated, the fourth layer 124 includes the second heater circuit 86, which includes a resistive heating coil 240 and a temperature sensor 242.

The resistive coil 240 is coupled to first and second conductors 244, 246, which are routed through third and fourth plated thru holes 248, 250 of the first plurality of plated thru holes 220. It should be noted that the positions of the first plurality of plated thru holes 220 of the fourth layer 124 may correspond to the respective positions of the first plurality of plated thru holes 190 of the first layer 118. Accordingly, because the first conductor 244 is routed through the third plated thru hole 248, which corresponds to the same position of the first plated thru hole 186 of FIG. 5, the first conductor 244 and the first conductor first conductor 182 may be the same, may be coupled to one another, or may be coupled to the same power source.

The temperature sensor 242 may be any temperature sensor capable of generating a signal in response to a temperature of the ion detection system 16. Thus, in certain embodiments, the temperature sensor 242 may be a thermocouple, such as a K-, E-, J-, N-, B-, R-, S-, T-, C- or M-type thermocouple. The temperature sensor 242 is illustrated as being coupled to third and fourth conductors 252, 254, which are routed through fifth and sixth plated thru holes 256, 258. The third and fourth conductors 252, 254 may electrically couple the temperature sensor 242 to the circuit board 49. By way of non-limiting example, the controller 44 may control/adjust an amount of thermal energy generated by the resistive coil 240 in response to a temperature detected by the temperature sensor 242 (e.g., in response to receiving signals indicative of a temperature). Such temperature maintenance may be desirable to reduce temperature effects on ionization, ion filtering, and/or ion detection.

This written description uses examples to disclose the present subject matter, including the best mode, and also to enable any person skilled in the art to practice the present approaches, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A breath analysis system, comprising:
   a breath sample preparation system, comprising:
      a first inlet configured to receive a patient's expired breath comprising an analyte of interest;
      a second inlet configured to receive a carrier gas, wherein the first and second inlets are configured such that the patient's expired breath only enters the breath sample preparation system via the first inlet and the carrier gas only enters the breath sample preparation system via the second inlet; and
      a mixing chamber configured to mix at least a portion of the patient's expired breath with the carrier gas to generate a gas mixture; and an ion detection system operatively coupled to the breath sample preparation system, comprising:
- a first pair of layers each comprising a heater circuit configured to maintain a temperature of the ion detection system within a range;
- a second pair of layers positioned between the first pair of layers, each of the second pair of layers comprising a detector circuit, wherein the second pair of layers form at least a portion of a gas path configured to flow the gas mixture, and wherein the respective detector circuits of the second pair of layers form an ion detector configured to detect an ionized analyte of interest within the gas path; and
- an ionization source mounted through at least one of the first pair of layers or at least one of the second pair of layers, or any combination thereof, and disposed along the gas path upstream from the detector, and wherein the ionization source is configured to ionize at least the analyte of interest within the gas mixture to produce the ionized analyte of interest; and
- wherein all layers of the first pair of layers and the second pair of layers are parallel with one another.

2. The system of claim 1, wherein the detector comprises one or more electrometers configured to generate an electric current in response to an amount of the ionized analyte.

3. The system of claim 1, wherein each of the second pair of layers comprises an ion filter circuit, wherein the respective ion filter circuits of the second pair of layers form an ion filter disposed along the gas path between the ionization source and the ion detector, and the ion filter is configured to separate different ionized molecules of the gas mixture from one another.

4. The system of claim 3, wherein the respective ion filter circuits of the second pair of layers are configured to generate a direct current (DC) electric field such that the molecules ionized by the ionization source flow through the gas path and reach the ion detector at respective times characteristic of their respective mobilities within the DC electric field.

5. The system of claim 3, wherein the respective ion filter circuits of the second pair of layers generate a radiofrequency (RF) electric field such only ionized molecules with predetermined characteristics flow through the RF electric field and are able to reach the ion detector.

6. The system of claim 5, wherein the respective ion filter circuits of the second pair of layers generate a DC electric field such that the ionized molecules having the predetermined characteristics flow through the RF and DC electric field and reach the ion detector at respective times characteristic of their respective mobilities within the RF and DC electric field.

7. The system of claim 1, wherein the respective heater circuits of the first pair of layers extend along the full length of the gas path.

8. The system of claim 1, wherein the ionization source comprises a UV lamp, a β-emitter, a corona discharge source, a flame ionization source, or any combination thereof.

9. The system of claim 1, wherein the ionization source is tuned to an ionization potential of the analyte of interest.

10. The system of claim 9, wherein the analyte of interest comprises an anesthetic agent, a metabolite of an anesthetic agent, or a combination thereof.

11. The system of claim 1, wherein the preparation system comprises one or more filters disposed between the first inlet and the mixing chamber, or the second inlet and the mixing chamber, or a combination thereof, and the one or more filters are configured to remove moisture, carbon dioxide ($CO_2$), sputum, food particles, interfering compounds, or a combination thereof, from the patient's expired breath, or from the carrier gas, or a combination thereof.

12. The system of claim 1, comprising a transfer path coupling the breath sample preparation system with the ion detection system, and the transfer path is configured to heat the gas mixture, maintain a temperature of the gas mixture, or a combination thereof.

13. The system of claim 1, comprising a pump configured to motivate the gas mixture through the gas path.

14. A breath analysis system, comprising:
an ion detection system, comprising:
- an inlet configured to receive a gas mixture having an analyte of interest expired by a patient;
- a first pair of layers each comprising a heater circuit configured to maintain a temperature of the ion detection system within a range;
- a second pair of layers between the first pair of layers and comprising an ion detector, wherein two of the second pair of layers form at least a portion of a gas path fluidly coupled to the inlet and configured to flow the gas mixture, and wherein the ion detector is configured to detect an ionized analyte of interest within the gas path; and
- an ionization source mounted through at least one of the first pair of layers or at least one of the second pair of layers, or any combination thereof, disposed along the gas path upstream from the detector, and wherein the ionization source is configured to ionize molecules within the gas mixture, the molecules comprising at least the analyte of interest; and
- wherein all layers of the first pair of layers and the second pair of layers are parallel with one another.

15. The system of claim 14, wherein the ion detection system comprises a substrate having the inlet.

16. The system of claim 15, wherein the substrate is a printed circuit board.

17. The system of claim 14, wherein the ion detection system is integrated onto a single circuit board comprising a processor configured to control the operation of at least the ion detection system.

18. The system of claim 14, wherein the second pair of layers comprise an ion filter disposed along the gas path between the ionization source and the ion detector, and the ion filter is configured to separate different ionized molecules of the gas mixture from one another.

19. The system of claim 18, wherein the ion filter is configured to generate a radiofrequency (RF) electric field, or a DC electric field, or a combination thereof.

20. The system of claim 14, comprising a breath sample preparation system configured to prepare a patient's expired breath for analysis by the ion detection system, comprising:
- a breath inlet configured to receive the patient's expired breath comprising the analyte of interest;
- a carrier gas inlet configured to receive a carrier gas;
- a mixing chamber configured to mix at least a portion of the patient's expired breath with the carrier gas to generate the gas mixture; and
- an outlet configured to fluidly couple the preparation system to the inlet of the ion detection system such that the gas mixture is able to flow from the preparation system to the ion detection system.

21. The system of claim 20, wherein the preparation system comprises a filter disposed between the breath inlet and the mixing chamber, wherein the filter is configured to remove moisture, carbon dioxide ($CO_2$), sputum, food particles, interfering compounds, or a combination thereof, from the patient's expired breath.

22. The system of claim 20, comprising a temperature sensor configured to monitor a temperature of the gas mixture before ionization by the ionization source, or a humidity sensor configured to monitor a moisture level of the gas mixture before ionization by the ionization source, or a combination thereof.

23. A breath analysis system, comprising:
an ion detection system, comprising:
a plurality of substrate layers comprising one or more thru holes configured to enable the breath analysis system to integrate onto a circuit board, wherein the plurality of substrate layers comprises:
an inlet configured to receive a gas mixture having an analyte of interest from a patient's expired breath;
a first pair of layers each comprising a heater configured to maintain a temperature of the ion detection system within a range; and
a second pair of layers disposed between the first pair of layers, each layer of the second pair of layers comprising an ion filter circuit and a detector circuit, wherein the second pair of layers form at least a portion of a gas path fluidly coupled to the inlet, wherein the gas path is configured to flow the gas mixture toward an outlet of the ion detection system, wherein the respective ion filter circuits of the second pair of layers form an ion filter coupled to an inner surface of the plurality of substrate layers along the gas path, the ion filter being configured to separate an ionized analyte of interest from other components of the gas mixture, and wherein the respective detector circuits of the second pair of layers form an ion detector coupled to the inner surface of the plurality of substrate layers along the gas path and downstream from the ion filter, wherein the ion detector is configured to generate a signal in response to detecting the presence of the ionized analyte of interest within the gas path; and
an ionization source coupled to the plurality of substrate layers and disposed along the gas path, wherein the ionization source is configured to ionize at least the analyte of interest within the gas mixture to produce the ionized analyte of interest; and
wherein all layers of the first pair of layers and the second pair of layers are parallel with one another.

24. The system of claim 23, comprising a breath sample preparation system configured to prepare the patient's expired breath for analysis by the ion detection system, comprising:
a breath inlet configured to receive the patient's expired breath;
a carrier gas inlet configured to receive a carrier gas;
a mixing chamber configured to mix at least a portion of the patient's expired breath with the carrier gas to generate the gas mixture; and
an outlet configured to fluidly couple the preparation system to the inlet of the ion detection system such that the gas mixture is able to flow from the preparation system to the ion detection system.

25. The system of claim 24, wherein the preparation system comprises a filter disposed between the breath inlet and the mixing chamber, wherein the filter is configured to remove moisture, carbon dioxide ($CO_2$), sputum, food particles, interfering compounds, or a combination thereof, from the patient's expired breath.

26. The system of claim 23, wherein the ion detection system comprises a temperature sensor coupled to at least one of the plurality of substrate layers, wherein the heater and the temperature sensor are-configured to enable temperature control of the gas mixture within the gas path to reduce temperature effects on ionization of the gas mixture and detection of the analyte of interest.

* * * * *